United States Patent [19]

Sano et al.

[11] Patent Number: 5,637,490
[45] Date of Patent: Jun. 10, 1997

[54] α-1,3/4-FUCOSIDASE GENE

[75] Inventors: Mutsumi Sano, Otsu; Yuka Takabatake, Nagoya; Masanori Mitta, Tsuzuki-gun; Ikunoshin Kato, Uji, all of Japan

[73] Assignee: Takara Shuzo Co., Ltd., Kyoto-fu, Japan

[21] Appl. No.: 442,884

[22] Filed: May 17, 1995

[30]     Foreign Application Priority Data

May 18, 1994   [JP]   Japan .................................. 6-127109

[51] Int. Cl.$^6$ .............................. C12N 9/26; C12N 1/21; C12N 15/63; C07H 21/04
[52] U.S. Cl. .................. 435/201; 435/252.3; 435/320.1; 536/23.7
[58] Field of Search ............................... 435/201, 252.3, 435/320.1; 536/23.7

[56]            References Cited

FOREIGN PATENT DOCUMENTS

95/08645   3/1995   WIPO .

OTHER PUBLICATIONS

Fisher, K.J. et al. (1989) "Isolation and sequence analysis of a cDNA encoding rat liver alpha-fucosidase" Biochem. J. 264:695–701 1989.

Alberts, B. et al. Molecular Biology of the Cell, Second Edition. New York: Garland Publ. Inc. 1989, pp. 265–266 1989.

Fukushima, H. et al. (1985) "Molecular cloning of a cDNA for human alpha–L–fucosidase" Proc. Nat'l. Acad. Sci., USA. 82:1262–1265 Feb. 1985.

Muller–Taubenberger, A. et al. (1989) "A developmentally regulated gene product from Dictyostelium discoideum shows high homology to human alpha–L–fucosidase" FEBS Lett. 246(1,2):185–192 Mar. 1989.

Sano et al., "Purification and Characterization of α–L–Fucosidase from Strepomyces Species", The Journal of Biological Chemistry, vol. 267, No. 3, pp. 1522–1527, Jan. 25, 1992.

Midor Ogata–Arakawa et al., "α–L–Fucoisidases from Almond Emulsin: Characterization of the Two Enzymes with Different Specificities", Archives of Biochemistry and Biophysics 181, pp. 353–358, (1977).

Michael J. Imber et al., "Purification of an Almond Emulsin Fucosidase on Cibacron Blue–Sepharose and Demonstration of Its Activity Toward Fucose–Containing Glycoproteins", The Journal of Biological Chemistry vol. 257, No. 14, Issue of Jul. 25, 1982 pp. 8205–8210.

Peter Scudder et al., "The Isolation by Ligand Affinity Chromatography of a Novel Form of α–L–Fucosidase from Almond", The Journal of Biological Chemistry, vol. 265, No. 27, Issue of Sep. 25, 1990, pp. 16472–16477.

Mutsumi Sano et al., "Purification and Characterization of α–L–Fucosidase From Streptomyces Species", vol. 267, No. 3, Issue of Jan. 25, 1992, pp. 1522–1527.

*Primary Examiner*—Robert A. Wax
*Assistant Examiner*—Kawai Lau
*Attorney, Agent, or Firm*—Wenderoth, Lind & Ponack

[57]            ABSTRACT

An isolated α-1,3/4-fucosidase gene is provided which codes for an α-1,3/4-fucosidase enzyme. The isolated gene codes for the fucosidase enzyme having the amino acid sequence shown in SEQ ID No. 1. The gene may have the DNA sequence shown in SEQ ID No. 2. A process for producing the fucosidase enzyme is also provided, which comprises cultivating a transformant into which a recombinant plasmid containing the α-1,3/4-fucosidase gene according to the invention has been introduced to produce the fucosidase enzyme encoded thereby, and harvesting the fucosidase enzyme from the culture.

10 Claims, 1 Drawing Sheet

FIG. 1

A (2.3 kbp, PstI fragment)

B (1.9 kbp, SalI fragment)

α-1,3/4-FUCOSIDASE GENE

INDUSTRIAL FIELD OF UTILIZATION

This invention relates to a nucleotide sequence coding for an α-1,3/4-fucosidase which is useful in the sugar chain technology for analyzing, for example, the structures and the functions of sugar chains and glycoproteins and an amino acid sequence thereof. This invention further relates to a process for industrial production of an α-1,3/4-fucosidase with the use of a transformant into which a recombinant plasmid containing the α-1,3/4-fucosidase gene has been introduced.

PRIOR ART TECHNOLOGY

L-Fucose occurs mainly at the nonreducing end of sugar chains as a constituting sugar of so-called glycoconjugates such as glycoproteins, glycolipids and glycosaminoglycans. Fucose with an α-1,3/4 bond is contained in Lewis blood group antigens, tumor-associated antigens or ligands of selectins which are cell adhesion molecules. α-1,3/4-Fucosidase has been employed as a reagent which is highly useful in analyzing the structures or the functions of these sugar chains.

Known examples of α-1,3/4-fucosidase include α-fucosidase I [Archives of Biochemistry and Biophysics, 181, 353–358 (1977); Journal of Biological Chemistry, 257, 8205–8210 (1982)] and α-fucosidase III [Journal of Biological Chemistry, 265, 16472–16477 (1990)] from almond and one from Streptomyces [Journal of Biological Chemistry, 267, 1522–1527 (1992)].

PROBLEMS TO BE SOLVED BY THE INVENTION

However the method for obtaining α-fucosidase from almond meal or almond emulsin has such a disadvantage that almond contains various glycosidases and, therefore, it is highly difficult to completely separate the target a-fucosidase from these glycosidases and purify this enzyme to a high extent. In the method for obtaining α-1,3/4-fucosidase by cultivating an actinomycete belonging to the genus Streptomyces, on the other hand, it is required to add expensive L-fucose to the medium in order to induce the production of the enzyme. This method suffers from an additional problem that other enzymes including protease and lacto-N-biosidase are also formed and it is difficult to isolate and purify the target α-fucosidase therefrom. Accordingly it has been required to establish a process for producing α-1,3/4-fucosidase of a higher purity at a lower cost. Although there have been reported methods for purifying α-1,3/4-fucosidase from almond and an actinomycete belonging to the genus Streptomyces as described above, neither the amino acid sequence nor the gene structure of α-1,3/4-fucosidase has been clarified so far.

Also there has been disclosed no industrially advantageous method for producing α-1,3/4-fucosidase. Accordingly, the identification of the gene of α-1,3/4-fucosidase makes it possible to produce this enzyme in an uncontaminated and highly pure state by genetic engineering. Also it becomes possible to produce the enzyme which is useful in the glycotechnology for analyzing, for example, the structures and the functions of sugar chains and glycoproteins. Furthermore, the identification of the DNA sequence of this enzyme makes it possible to search genes of enzymes analogous thereto which are different therefrom in sequence but expected to have similar enzymatic activities. In addition, the amino acid sequence corresponding to the DNA sequence of this enzyme is useful in the preparation of an antibody for this enzyme.

It is an object of the present invention to provide an α-1,3/4-fucosidase gene, the DNA sequence thereof, the amino acid sequence thereof and a process for production of the α-1,3/4-fucosidase by genetic engineering.

MEANS TO SOLVE THE PROBLEMS

In summary, the first aspect of the present invention relates to an isolated α-1,3/4-fucosidase gene. In particular, it provides an α-1,3/4-fucosidase gene which codes for a fraction having an α-1,3/4-fucosidase enzymatic activity and corresponding to an amino acid sequence shown by SEQ ID NO. 1 or a part of the same and, among all, an α-1,3/4-fucosidase gene having a DNA sequence shown by SEQ ID NO. 2 and an α-1,3/4-fucosidase gene which can be hybridized with the above-mentioned gene corresponding to the amino acid sequence shown by the SEQ ID NO. 1 or a part of the same. The second aspect of the present invention relates to a process for industrial production of an α-1,3/4-fucosidase. In particular, it provides a process for production of an α-1,3/4-fucosidase by cultivating a transformant, into which a recombinant plasmid containing the α-1,3/4-fucosidase gene has been introduced, and harvesting the α-1,3/4-fucosidase from the culture.

The invention will be further described below, by referring partly to FIG. 1 which is a diagram showing the correlation between PstI and SalI fragments and restriction enzyme maps wherein A is the restriction enzyme map of the PstI fragment of 2.3 kb in size while B is the restriction enzyme map of the SalI fragment of 1.9 kb in size.

In order to acquire the above-mentioned α-1,3/4-fucosidase gene, the present inventors highly purified α-1,3/4-fucosidase from Streptomyces sp. 142 and determined the N-terminal amino acid sequence and partial amino acid sequences of the same. Based on the information about these amino acid sequences, they subsequently effected PCR in accordance with the conventional method by using synthetic oligonucleotide primers. However they could not succeed in the acquisition of the α-1,3/4-fucosidase gene, and neither could they with the use of these primers as a probe. Thus they conducted extensive studies on various conditions for effecting PCR. As a result, they succeeded in the amplification of a part of the α-1,3/4-fucosidase gene by using a specific pair of synthetic primers under specific conditions. By using the gene thus amplified as a probe, they isolated the target gene and determined the nucleotide sequence thereof. Further they constructed a recombinant plasmid capable of expressing active α-1,3/4-fucosidase in a microorganism. Then they successfully produced the α-1,3/4-fucosidase by using the microorganism which had been transformed by the above-mentioned plasmid, thus completing the present invention.

Now, the present invention will be described in greater detail by citing Streptomyces sp. 142 by way of example. This strain is described in Japanese Patent Laid-Open No. 98583/1991 as Streptomyces sp. 142 and has been deposited since Feb. 17, 1994 under the Budapest Treaty as FERM BP-4569 at National Institute of Bioscience and Human-Technology, Agency of Industrial Science and Technology, of 1–3, Higashi 1-chome, Tsukuba-shi, Ibaraki-ken 305, Japan.

First, a crude enzyme solution is prepared from Streptomyces sp. 142 and the α-1,3/4-fucosidase is purified to a high extent by various chromatographic techniques.

To obtain the information on the partial amino acid sequences of the α-1,3/4-fucosidase purified, the purified α-1,3/4-fucosidase, obtained by the method described in, for example, Journal of Biological Chemistry, 267, 1522–1527 (1992), may be subjected directly to the Edman degradation and analysis of the amino acid sequences thereof. Alternatively, it may be subjected to the limited hydrolysis by using a protein hydrolase with a high specificity followed by the separation and purification of the peptide fragments thus obtained by reversed-phase HPLC. It is effective to analyze the amino acid sequences of the purified peptide fragments. On the basis of the information on these partial amino acid sequences, the α-1,3/4-fucosidase gene can be cloned generally by the PCR method or by the hybridization method.

1) PCR Method With the Use of Cassette DNA

A genomic DNA extracted from Streptomyces sp. 142 by a conventional method is digested with appropriate restriction enzymes and then ligated to a synthetic DNA (cassette DNA) having a known sequence. By using the product thus obtained as a template, PCR is effected with the use of synthetic oligonucleotide primers, which have been designed by a conventional method depending on the information about the partial amino acid sequences, and synthetic oligonucleotide primers (cassette primers) complementary to the cassette DNA. Thus the target DNA fragment can be amplified. As the cassette DNA or the cassette primers, use can be made of, for example, those manufactured by Takara Shuzo Co., Ltd. The cassette DNA contains sequences corresponding to 2 cassette primers. It is known that the target DNA fragment can be effectively amplified by carrying out the first PCR by using the primer located far from the restriction enzyme site and then carrying out the second PCR by using a portion of the reaction mixture of the first PCR as a template with the use of the primer located close to the restriction enzyme site. The present inventors attempted to acquire the gene of the present invention by this method. First, synthetic nucleotide primers FSE-1 (SEQ ID NO. 5) and 57R (SEQ ID NO. 6) are synthesized respectively from the N-terminal sequence N-1 (SEQ ID NO. 3) and the partial amino acid sequence 57 (SEQ ID NO. 4). The genomic DNA extracted from Streptomyces sp. 142 in a conventional manner is digested with restriction enzymes Sau3AI, BamHI, PstI and SalI and the corresponding cassette DNAs (manufactured by Takara Shuzo Co., Ltd.) are ligated thereto respectively. By using them as a template, PCR is effected with the use of a combination of FSE-1 with C1 primer (manufactured by Takara Shuzo Co., Ltd.) and another combination of 57R with C1 primer. The PCR is effected in accordance with a method described in PCR Technology, edited by Erlich, published by Stockton Press (1989). For example, it can be effected by using GeneAmp PCR Reagent Kit (manufactured by Takara Shuzo Co., Ltd.). The reaction is performed, for example, for 30 cycles with each cycle consisting of 30 seconds at 94° C., 1 minute at 55° C. and 1 minute at 72° C. By using a portion of the reaction mixture, PCR is further effected under the same conditions with the use of a combination of FSE-1 with C2 primer (manufactured by Takara Shuzo Co., Ltd.) and another combination of 57R with C2 primer. When the reaction mixture is analyzed by agarose gel electrophoresis, the α-1,3/4-fucosidase gene of the present invention shows no DNA fragment specifically amplified. Thus it is impossible to clone the α-1,3/4-fucosidase gene of the present invention by this method.

2) Common PCR Method

The target DNA fragment can be amplified by effecting PCR with the use of synthetic oligonucleotide primers which have been designed on the basis of the information on the partial amino acid sequences. First, a synthetic oligonucleotide primer 57F (SEQ ID NO. 7) is synthesized from the partial amino acid sequence 57 (SEQ ID NO. 4), while nucleotide primers 39F (SEQ ID NO. 9) and 39R (SEQ ID NO. 10) are synthesized from the partial amino acid sequence 39 (SEQ ID NO. 8), and oligonucleotide primers 45F (SEQ ID NO. 12) and 45R (SEQ ID NO. 13) are synthesized from the partial amino acid sequence 45 (SEQ ID NO. 11).

Then the primers including FSE-1 (SEQ ID NO. 5) and 57R (SEQ ID NO. 6) as described in the above 1) are used in the combinations as specified in Table 1 and PCR is effected with the use of the genomic DNA of Streptomyces sp. 142 as a template.

TABLE 1

|       | 57R | 39R | 45R |
|-------|-----|-----|-----|
| FSE-1 | (1) | (2) | (3) |
| 57F   | —   | (4) | (5) |
| 39F   | (6) | —   | (7) |
| 45F   | (8) | (9) | —   |

The PCR is performed, for example, for 35 cycles with each cycle consisting of 30 seconds at 94° C., 1 minute at 50° C. and 1.5 minutes at 72° C. When the reaction mixture is analyzed by agarose gel electrophoresis, amplified DNA fragments of 200 bp and 900 bp in size are observed respectively in a combination of FSE-1 (SEQ ID NO. 5) with 45R (SEQ ID NO. 13) [i.e., the combination (3) in Table 1] and a combination of 45F (SEQ ID NO. 12) with 39R (SEQ ID NO. 10) [i.e., the combination (9) in Table 1]. Other combinations show either no amplification or a number of amplified products. Although the nucleotide sequences of the DNA fragments specifically amplified by using the combinations (3) and (9) in Table 1 are determined by a method commonly employed in the art, no sequence seemingly corresponding to the target gene can be found out other than the sequences of the synthesized DNAs.

3) Synthetic DNA Hybridization Method

There has been generally used a method comprising designing synthetic oligonucleotides depending on the information about partial amino acid sequences and detecting the target DNA through hybridization. The present inventors attempted to detect the α-1,3/4-fucosidase gene of the present invention by this method.

As a probe for Southern hybridization, use is made of the synthetic oligonucleotides FSE (SEQ ID NO. 5) and 39F (SEQ ID NO. 7) described in the PCR method of the above 2) and synthetic oligonucleotides 28F (SEQ ID NO. 15) and 32R (SEQ ID NO. 17) synthesized respectively from the partial amino acid sequences 28 (SEQ ID NO. 14) and 32 (SEQ ID NO. 16). The genomic DNA of Streptomyces sp. 142 is completely digested with a restriction enzyme BamHI, PstI, SacI or SalI, separated by agarose gel electrophoresis and blotted onto a nylon membrane in a conventional manner. The hybridization can be effected under the conditions commonly employed in the art. For example, the nylon membrane is blocked in a prehybridization solution containing 6×SSC, 0.5% of SDS, 5×Denhardt's and 100 μg/ml of salmon sperm DNA at 65° C. Then each synthetic oligonucleotide labeled with $^{32}P$ is added and the resulting mixture is kept at 40° C. overnight. The nylon membrane is washed with 2×SSC containing 0.1% of SDS at 50° C. for 30 minutes. Then DNA fragments hybridizable with the synthetic oligonucleotide probes are detected by autoradiography. No DNA fragment hybridizable with the probe 39F (SEQ ID NO. 7) is detected, while other probes FSE-1 (SEQ ID NO. 5), 28F (SEQ ID NO. 15) and 32R (SEQ ID NO. 17) each shows a number of bands on the lane of each restriction enzyme digestion product. It is therefore impossible to specify the target α-1,3/4-fucosidase gene.

As described above, it is highly difficult in the conventional method to clone the α-1,3/4-fucosidase gene of the present invention from the genomic DNA of Streptomyces sp. 142 by the conventional method. When the genomic DNA of Streptomyces sp. 142 is used as a template, the progress of the polymerase chain reaction is inhibited or nonspecific annealing occurs. Thus it is anticipated that the PCR method suffers from the inhibition of amplification or the amplification of nonspecific DNA fragments while the hybridization method suffers from the formation of nonspecific hybrids. By taking these points into consideration, the present inventors effected the PCR under such conditions as to avoid the inhibition of the extension of DNA strands due to the formation of the secondary structure and minimize nonspecific annealing.

Namely, dGTP employed as the substrate in the PCR is replaced by its derivative 2'-deoxy-7-deazaguanosine triphosphate ($dc^7GTP$) and the reaction is effected at an elevated annealing temperature of 60° C. By using a portion of this reaction mixture as a template, the second reaction is carried out by using a usual substrate containing dGTP. Thus they have found out that a part of the target α-1,3/4-fucosidase gene is amplified for the first time with the use of a specific combination of primers.

Now this process will be described in greater detail. In addition to the synthetic oligonucleotide primers described in the above 2), synthetic oligonucleotide primers 28R (SEQ ID NO. 18) and 32F (SEQ ID NO. 19) designed respectively from the partial amino acid sequences 28 (SEQ ID NO. 14) and 32 (SEQ ID NO. 16) are synthesized. By using the genomic DNA of Streptomyces sp. 142 as a template, PCR is effected with the use of the combinations of the primers as specified in Table 2.

TABLE 2

|      | 28R  | 32R  | 39R  | 45R  | 57S  |
|------|------|------|------|------|------|
| FSE-1 | (1)  | (2)  | (3)  | (4)  | (5)  |
| 28F  | —    | (6)  | (7)  | (8)  | (9)  |
| 32F  | (10) | —    | (11) | (12) | (13) |
| 39F  | (14) | (15) | —    | (16) | (17) |
| 45F  | (18) | (19) | (20) | —    | (21) |
| 57F  | (22) | (23) | (24) | (25) | —    |

The PCR is effected by, for example, using GeneAmp PCR Reagent Kit and using a mixture of dATP, dCTP, dTTP, dGTP and $dc^7GTP$ as a substitute for the dNTP mixture for 25 cycles with each cycle consisting of 30 seconds at 94° C., 1 minute at 60° C. and 2 minutes at 72° C. By using a portion of this reaction mixture as a template and the usual dNTP mixture as a substrate, the PCR is performed again with the same cycles. A part of this reaction mixture is analyzed by agarose gel electrophoresis. Separately, a portion of the first PCR mixture is used as a template and the PCR is effected by adding one of the primers alone to thereby examine the DNA fragments amplified by using each of the primers alone. Table 3 shows the DNA fragments thus amplified by the PCR excluding those amplified by using a single primer.

TABLE 3

|       | 28R | 32R | 39R | 45R | 57R |
|-------|-----|-----|-----|-----|-----|
| FSE-1 | 0   | 1   | 0   | 0   | 1   |
| 28F   | —   | 0   | 0   | 0   | 3   |
| 32F   | 1   | —   | 0   | 0   | 1   |
| 39F   | 0   | 0   | —   | 0   | 0   |
| 45F   | 1   | 1   | 0   | —   | 2   |
| 57F   | 1   | 0   | 0   | 0   | —   |

The nucleotide sequences of these DNA fragments are determined by a method commonly employed in the art such as the dideoxy chain terminator method. Thus a sequence corresponding to the partial amino acid sequence of α-1,3/4-fucosidase is found out in a region following the primer sequence of the DNA fragment (140 bp) amplified by using the combination of 45F-32R [i.e., the combination (19) in Table 2]. Thus a part of the target α-1,3/4-fucosidase gene can be successfully obtained.

The genomic DNA of Streptomyces sp. 142 is digested with appropriate restriction enzymes. Then hybridization is effected by using the above-mentioned PCR product [i.e., the DNA fragment (140 bp) amplified by using the combination 45F-32R; SEQ ID NO. 20] as a probe. Thus a band hybridizable specifically with the probe can be detected. A DNA fragment corresponding to the band thus detected is extracted from the gel, purified and integrated into a plasmid vector by a method commonly employed in the art. As the plasmid vector, use can be made of publicly known ones such as pUC18, pUC19, pUC119 and pTV118N, though the present invention is not restricted thereto.

Next, the recombinant plasmid is introduced into a host to thereby transform the host. When Escherichia coli is to be used as the host, either a wild strain or a variant may be selected therefor, so long as it can undergo transformation. The introduction may be effected by a method commonly employed in the art, for example, the one described in Molecular Cloning, A Laboratory Manual, T. Maniatis et al., Cold Spring Harbor Laboratory (1982).

After introducing the target DNA fragment into the host, colonies having an alien gene introduced thereinto can be screened depending on the properties of the plasmid vector, for example, in the case of pUC19, by selecting colonies showing a tolerance for ampicillin or those showing a tolerance for ampicillin and having a white color on a plate containing ampicillin, 5-bromo-4-chloro-3-indolyl-β-D-galactoside (X-Gal) and isopropyl-β-D-thiogalactopyranoside (IPTG). Subsequently, colonies having a vector containing the target DNA fragment are screened from among the above-mentioned ones. The screening may be performed through colony hybridization or plaque hybridization selected depending on the vector. It is also possible to use take PCR method therefor. When the vector containing the target DNA fragment is screened, the nucleotide sequence of the target DNA fragment inserted into this vector can be determined by a common method such as the dideoxy chain terminator method. The nucleotide sequence thus determined is compared with the N-terminal analysis data, the partial amino acid sequences, the molecular weight, etc. of α-1,3/4-fucosidase. Thus the structure of the α-1,3/4-fucosidase gene and the full amino acid sequence of α-1,3/4-fucosidase can be clarified. An example of the nucleotide sequence thus obtained is shown by SEQ ID NO. 2 and an amino acid sequence which can be coded for by this nucleotide sequence is shownby SEQ ID NO. 1.

The host is transformed by the vector containing the target α-1,3/4-fucosidase gene and then the obtained transformant is cultivated under the conditions commonly employed. Thus a polypeptide or a protein having the α-1,3/4-fucosidase activity can be produced. It is sometimes possible to produce this polypeptide in the form of an inclusion body. To give an expression vector, the target α-1,3/4-fucosidase gene may be connected to a vector capable of expressing the same in an appropriate host.

As the host, use can be made of microorganisms, animal cells or plant cells. The expression can be ascertained by, for example, assaying the α-1,3/4-fucosidase activity. The activity can be assayed by, for example, the method described in Journal of Biological Chemistry, 267, 1522–1527 (1992) with the use of the cell extract of a recombinant of *Escherichia coli* as an enzyme solution. When the expression of the target α-1,3/4-fucosidase is ascertained, the optimum conditions for the expression are examined.

The α-1,3/4-fucosidase may be purified from the culture of the transformant by a conventional method. When *Escherichia coli* is used as the host, for example, the cells are collected by centrifugation after the completion of the cultivation. Then the cells are disrupted by, for example, sonication and soluble fractions are collected by centrifugation, etc. Then these fractions are purified by various chromatographic techniques such as ion exchange chromatography, gel filtration chromatography, hydrophobic chromatography or affinity chromatography. Thus an α-1,3/4-fucosidase specimen having a high purity can be obtained. When the polypeptide is obtained in the form of an inclusion body, insoluble fractions containing the inclusion body are collected. After washing, the inclusion body is solubilized with a protein-solubilizing agent commonly employed in the art (for example, urea or guanidine hydrochloride) and purified by various chromatographic techniques such as ion exchange chromatography, gel filtration chromatography, hydrophobic chromatography or affinity chromatography, if necessary. After refolding by dialysis, dilution, etc., the target α-1,3/4-fucosidase specimen sustaining its activity can be obtained. If required, this specimen is further purified by various chromatographic techniques. Thus a α-1,3/4-fucosidase specimen of an elevated purity can be obtained.

Further, it is expected that genes of all the enzymes, which are somewhat different from the above-mentioned enzyme in sequence but have similar activities, can be obtained by effecting hybridization under stringent conditions with the use of these genes thus obtained as a probe. The expression "stringent conditions" as used herein means the conditions as described below. That is to say, a nylon membrane having DNAs immobilized thereon is hybridized with a probe in a solution containing 6×SSC ("1×SSC" means 8.76 g of sodium chloride and 4.41 g of sodium citrate dissolved in 1 l of water), 1% of sodium lauryl sulfate, 100 µg/ml of salmon sperm DNA, 5×Denhardt's (containing 0.1% portions of bovine serum albumin, polyvinylpyrrolidone and ficoll) at 65° C. for 20 hours.

The target gene coding for α-1,3/4-fucosidase can be obtained by hybridization in, for example, the following manner. First, chromosomal DNAs obtained from a source of the target gene or cDNAs prepared from mRNAs with the use of a reverse transcriptase are connected to a plasmid or phage vector and introduced into a host to thereby prepare a library. Then this library is cultivated on a plate and colonies or plaques thus formed are transcribed onto a nitrocellulose or nylon membrane and the DNAs are immobilized on the membrane by a denaturation treatment. Subsequently this membrane is maintained at a given temperature in a solution containing a probe which has been labeled with $^{32}$P to thereby form hybrids between the DNAs and the probe. As the probe, a gene coding for the amino acid sequence shown by SEQ ID NO. 1 or a part of the same may be used. For example, a gene shown by SEQ ID NO. 2 or a part of the same is usable therefor. For example, genes coding for amino acid sequences shown by SEQ ID NOs. 3, 4, 8, 11, 14 and 16 or a part of the same may be used therefor. For example, a gene shown by SEQ ID NO. 20 or a part of the same may be used therefor. For example, the membrane having DNAs immobilized thereon is hybridized with the probe in a solution containing 6×SSC, 1% of sodium lauryl sulfate, 100 µg/ml of salmon sperm DNA, 5×Denhardt's (containing 0.1% portions of bovine serum albumin, polyvinylpyrrolidone and Ficoll) at 65° C. for 20 hours. After the completion of the hybridization, unspecifically adsorbed matters are washed away and clones forming hybrids with the probe are identified by autoradiography, etc. This procedure is repeated until a single clone forming the hybrids is obtained. The clone thus obtained has a gene coding for the target protein inserted therein.

The nucleotide sequence of the gene thus obtained is determined by, for example, the following manner to thereby ascertain whether it is the gene coding for the target α-1,3/4-fucosidase.

In the case of a clone obtained by the hybridization, the nucleotide sequence is determined in the following manner. When the transformant is *Escherichia coli*, it is cultivated in a test tube, etc. and the plasmid is extracted therefrom by a conventional method. Then the plasmid is cleaved with restriction enzymes and the insert is taken out and subcloned into M13 phage vector, etc. Then the nucleotide sequence is determined by the dideoxy method. When the transformant is a phage, the nucleotide sequence can be determined fundamentally through similar steps. The fundamental procedures from the cultivation to the determination of the nucleotide sequence are described in, for example, Molecular Cloning, A Laboratory Manual, T. Maniatis et al., Cold Spring Harbor Laboratory (1982).

In order to ascertain whether the obtained gene is the target one coding for α-1,3/4-fucosidase, the nucleotide sequence thus determined is compared with the α-1,3/4-fucosidase gene of the present invention and the amino acid sequence shown by SEQ ID NO. 1 to thereby clarify the gene structure and the amino acid sequence of the same.

When the obtained gene does not contain the full region coding for α-1,3/4-fucosidase, synthetic DNA primers are prepared based on the obtained gene and the missing region is amplified by PCR. Alternatively, the DNA library or the cDNA library is further screened by using a fragment of the obtained gene as a probe. Thus the nucleotide sequence of the full code region of the α-1,3/4-fucosidase hybridizable with the α-1,3/4-fucosidase gene of the present invention can be determined.

In order to obtain a polypeptide having the α-1,3/4-fucosidase activity by genetic engineering, the obtained α-1,3/4-fucosidase gene is first connected to an expression vector, which can express the gene in appropriate host cells such as *Escherichia coil*, *Bacillus subtilis*, Actinomyces, yeasts, animal cells, insect cells or plant cells, in a conventional manner. Then it is introduced into host cells to thereby form a transformant. By cultivating this transformant, the polypeptide having the α-1,3/4-fucosidase activity can be produced. Also, an α-1,3/4-fucosidase polypeptide free from any sugar chain can be expressed by using cells lacking in the ability to biologically synthesize a sugar chain (for example, procaryotes such as *Escherichia coli* and *Bacillus subtilis* or variant cells of yeasts, animals, insects and plants having lost the ability to biologically synthesize a sugar chain) as the host.

In some expression systems, the polypeptide expressed in the transformant is accumulated in the form of an insoluble matter (inclusion body). In such a case, this insoluble matter is recovered and solubilized with, for example, urea under mild conditions, and by removing the denaturing agent, the activity can be restored. The expression can be ascertained by assaying the α-1,3/4-fucosidase activity. The α-1,3/4-fucosidase activity can be assayed by, for example, the method described in Journal of Biological Chemistry, 267, 1522–1527 (1992).

The polypeptide having the α-1,3/4-fucosidase activity can be purified from the transformant by conventional chromatographic techniques. For example, when the target polypeptide is a solubilized one, the cells are disrupted and the supernatant is subjected to hydrophobic chromatography, ion-exchange chromatography, gel filtration chromatography, etc. Thus the target polypeptide can be obtained. When the expression product is accumulated in the form of an insoluble matter, the cells are disrupted and the precipitate is recovered and solubilized with a denaturing agent such as urea. Next, the denaturing agent is eliminated. After refolding, the target polypeptide having the α-1,3/4-fucosidase activity can be obtained by such chromatographic techniques as those described above.

The present invention provides the primary structure and the gene structure of α-1,3/4-fucosidase. Further, the present invention makes it possible to produce the α-1,3/4-fucosidase by genetic engineering. By using the genetic engineering process of the present invention, an α-1,3/4-fucosidase specimen having a high purity can be obtained at a low cost.

To further illustrate the present invention in greater detail, and not by way of limitation, the following Examples will be given.

EXAMPLE 1

Cloning of α-1,3/4-Fucosidase Structural Gene (1) Extraction and Purification of Genomic DNA Streptomyces sp. 142 (FERM BP-4569) producing α-1,3/4-fucosidase was inoculated into 20 ml of a medium (pH 7.0) containing 1% L-fucose, 0.01% yeast extract, 0.03% peptone, 0.05% $MgSO_4 7H_2O$ and 0.1% $KH_2PO_4$ and cultivated therein at 30° C. for 44 hours. After the completion of the cultivation, the cells were collected by centrifuging the culture medium, poured into liquid nitrogen and completely disrupted in a mortar. Then the disrupted cells were added in portions to 10 times as much an extractant buffer (10 mM Tris-HCl, 100 mM EDTA, 20 μg/ml RNaseA, 0.5% SDS, pH 8.0) under gentle stirring. After adding 100 μl of a 10 mg/ml solution of proteinase K thereto, the mixture was maintained at 37° C. for 1 hour. Then it was cooled to room temperature and an equal volume of a saturated solution of TE buffer (10 mM Tris-HCl, 1 mM EDTA, pH 8.0) in phenol/chloroform was added thereto. After gently stirring and centrifuging the mixture at 3,000 rpm for 10 minutes, the upper layer was recovered (this procedure will be referred to simply as "phenol extraction" hereinafter). After repeating this procedure twice, 0.6 equivalent volume of isopropyl alcohol was added to the aqueous layer followed by the centrifugation of the mixture at 14,000 rpm for 1 minute. Then it was rinsed with 70% ethanol and slightly air-dried. Thus about 440 μg of the genomic DNA was obtained.

(2) Determination of Partial Amino Acid Sequences of αa-1,3/4-Fucosidase

αa-1,3/4-Fucosidase, which had been purified by the method described in Journal of Biological Chemistry, 267, 1522–1527 (1992), was subjected directly to the gas-phase Edman degradation method in a conventional manner to thereby determine the N-terminal amino acid sequence N-1 (SEQ ID NO. 3) of the same. Further, the enzyme protein was pyridylethylated and digested with lysyl endopeptidase. The mixture of peptide fragments thus obtained was separated and purified by HPLC. Then the amino acid sequence of each peptide fraction was analyzed and thus partial amino acid sequences 57 (SEQ ID NO. 4), 39 (SEQ ID NO. 8), 45 (SEQ ID NO. 11), 28 (SEQ ID NO. 14) and 32 (SEQ ID NO. 16) were determined.

(3) Synthesis of Primers and Amplification by PCR

A synthetic oligonucleotide primer FSE-1 (SEQ ID NO. 5) was synthesized from the N-terminal amino acid sequence N-1 (SEQ ID NO. 3) determined in the above (2). Similarly, synthetic oligonucleotide primers 57F (SEQ ID NO. 7) and 57R (SEQ ID NO. 6) were synthesized from the partial amino acid sequence 57 (SEQ ID NO. 4); synthetic oligonucleotide primers 39F (SEQ ID NO. 9) and 39R (SEQ ID NO. 10) were synthesized from the partial amino acid sequence 39 (SEQ ID NO. 8); synthetic oligonucleotide primers 45F (SEQ ID NO. 12) and 45R (SEQ ID NO. 13) were synthesized from the partial amino acid sequence 45 (SEQ ID NO. 11); synthetic oligonucleotide primers 28F (SEQ ID NO. 15) and 28R (SEQ ID NO. 18) were synthesized from the partial amino acid sequence 28 (SEQ ID NO. 14); and synthetic oligonucleotide primers 32F (SEQ ID NO. 19) and 32R (SEQ ID NO. 17) were synthesized from the partial amino acid sequence 32 (SEQ ID NO. 16). The genomic DNA prepared in the above (1) was employed as a template, while primers were used in the combinations as listed in Table 2. Then PCR was effected in a reaction system of GeneAmp PCR Reagent Kit (manufactured by Takara Shuzo Co., Ltd.) containing 10 ng of the genomic DNA, which had been thermally denatured for 10 minutes, and 25 pmol portions of the synthetic oligonucleotide primers with the use of 1.2 mM (the final concentration, the same will apply hereinafter) dATP, 1.2 mM dCTP, 1.2 mM TTP, 0.9 mM dGTP and 0.3 mM $dc^7GTP$ (manufactured by Boehringer) as substitutes for the dNTP mixture. The volume of the reaction mixture was adjusted to 25 μl by adding 1.25 U Ampli Taq and sterilized water and the obtained mixture was subjected to amplification by using an automated gene amplifier (DNA Thermal Cycler, manufactured by Takara Shuzo Co., Ltd.). The reaction was performed for 25 cycles with each cycle consisting of 30 seconds at 94° C. (denaturation), 1 minute at 60° C. (annealing of the primers) and 2 minutes at 72° C. (synthesis reaction). Subsequently, PCR was effected again under the same conditions as those described above by using 1 μl of the reaction mixture obtained above as a template in 50 μl of a reaction system with the use of GeneAmp Reagent Kit and the usual dNTP mixture. A 10 μl portion of the reaction mixture was electrophoresed on a 3% agarose gel and the DNA was stained with ethidium bromide to thereby examine amplified DNA fragments. The above procedure was repeated using one of the primers alone to thereby examine the DNA fragments amplified by using each of the primers alone. Table 3 shows the DNA fragments thus amplified by the PCR excluding those amplified by using a single primer. The nucleotide sequences of these DNA fragments were determined by the dideoxy chain terminator method. As a result, a sequence corresponding to the partial amino acid sequence of α-1,3/

4-fucosidase was found out in a region following the primer sequence of the DNA fragment (140 bp) amplified by using the combination of 45F-32R [i.e., the combination (19) in Table 2]. Thus a part of the target α-1,3/4-fucosidase gene could be successfully obtained. This DNA fragment amplified by the PCR was named 45F-32R (SEQ ID NO. 20).

(4) Cloning of DNA Fragment Containing α-1,3/4-Fucosidase Gene in the Full Length 50 μg of the genomic DNA prepared in the above (1) was digested with 120 U portions of a restriction enzyme BamHI, PstI, SacI or SalI each for 2 hours at 37° C. Next, 60 U of each restriction enzyme was added and the reaction was continued for additional 4 hours. The reaction mixture was subjected to the phenol extraction and 10 μg of the DNA thus obtained was electrophoresed on a 0.7% agarose gel. After the completion of the electrophoresis, the DNA was transcribed onto a nylon membrane (Hybond-N$^+$, manufactured by Amersham) by the Southern blotting method (Idenshi Kenkyu-ho II, pp. 218–221, published by Tokyo Kagaku Dojin). As a probe for hybridization, the DNA fragment 45F-32R (SEQ ID NO. 20) obtained in the above (3) was employed.

5 pmol of this fragment was labeled with $^{32}$P by using MEGALABEL (manufactured by Takara Shuzo Co., Ltd.). By using the filter prepared above, prehybridization was effected at 65° C. for 3 hours in a solution containing 6×SSC ("1×SSC" means 8.77 g of sodium chloride and 4.41 g of sodium citrate dissolved in 1 l of water), 0.5% of SDS, 100 mg/ml of herring sperm DNA, 5×Denhardt's (containing 0.1% portions of bovine serum albumin, polyvinylpyrrolidone and ficoll). Subsequently, the labeled probe was added to give a concentration of 1 pmol/ml and hybridization was effected at 65° C. overnight. Then the filter was washed in 6×SSC at room temperature for 10 minutes, in 2×SSC and 0.1% SDS at room temperature for 10 minutes and in 0.2×SSC and 0.1% SDS at 50° C. for 1 hour and the excessive moisture was removed. Then a sensitized paper sheet was attached to the membrane and autoradiography was performed at −70° C. overnight.

As a result, bands hybridizable with the probe were observed at about 4.5 kb (in the case of the BamHI digestion product), at about 2.3 kb (in the case of the PstI digestion product), at about 10 kb (in the case of the SacI digestion product) and at about 1.9 kb (in the case of the SalI digestion product).

The PstI and SalI digestion products were used in the subsequent experiments since they could be conveniently handled. 10 μg of the genomic DNA which had been digested with the restriction enzymes was electrophoresed on a 0.7% agarose gel and the parts corresponding to the bands observed in the above-mentioned hybridization were cut off from the gel. After extracting and purifying by using EASYTRAP (manufactured by Takara Shuzo Co., Ltd.), the DNA fragments thus obtained were inserted into the PstI site or the SalI site of pUC19.

*Escherichia coli* JM109 was transformed by these plasmids and 200 to 1,000 colonies per plate were formed in three Petri dishes of 8.5 cm in diameter. Next, 200 colonies per restriction enzyme were selected from these plates and transcribed onto a nylon membrane (Hybond-N$^+$, manufactured by Amersham). After maintaining at 37° C. for 3 hours, the nylon membrane was treated successively on a filter paper moistened with a 0.5M solution of NaOH and a 1.5M solution of NaCl for 5 minutes (denaturation) and another filter paper moistened with a 0.5M Tris-HCl buffer (pH 7.0) and a 3M solution of NaCl for 5 minutes (neutralization) and rinsed with 2×SSC. By using this nylon membrane and the DNA fragment 45F-32R (SEQ ID NO. 20), hybridization was effected under the same conditions as those described above. As a result, one positive signal and two positive signals were obtained respectively from the PstI fragment and the SalI fragment. These *Escherichia coli* JM109 clones were named P54, S30 and S68 respectively.

Figure 1:
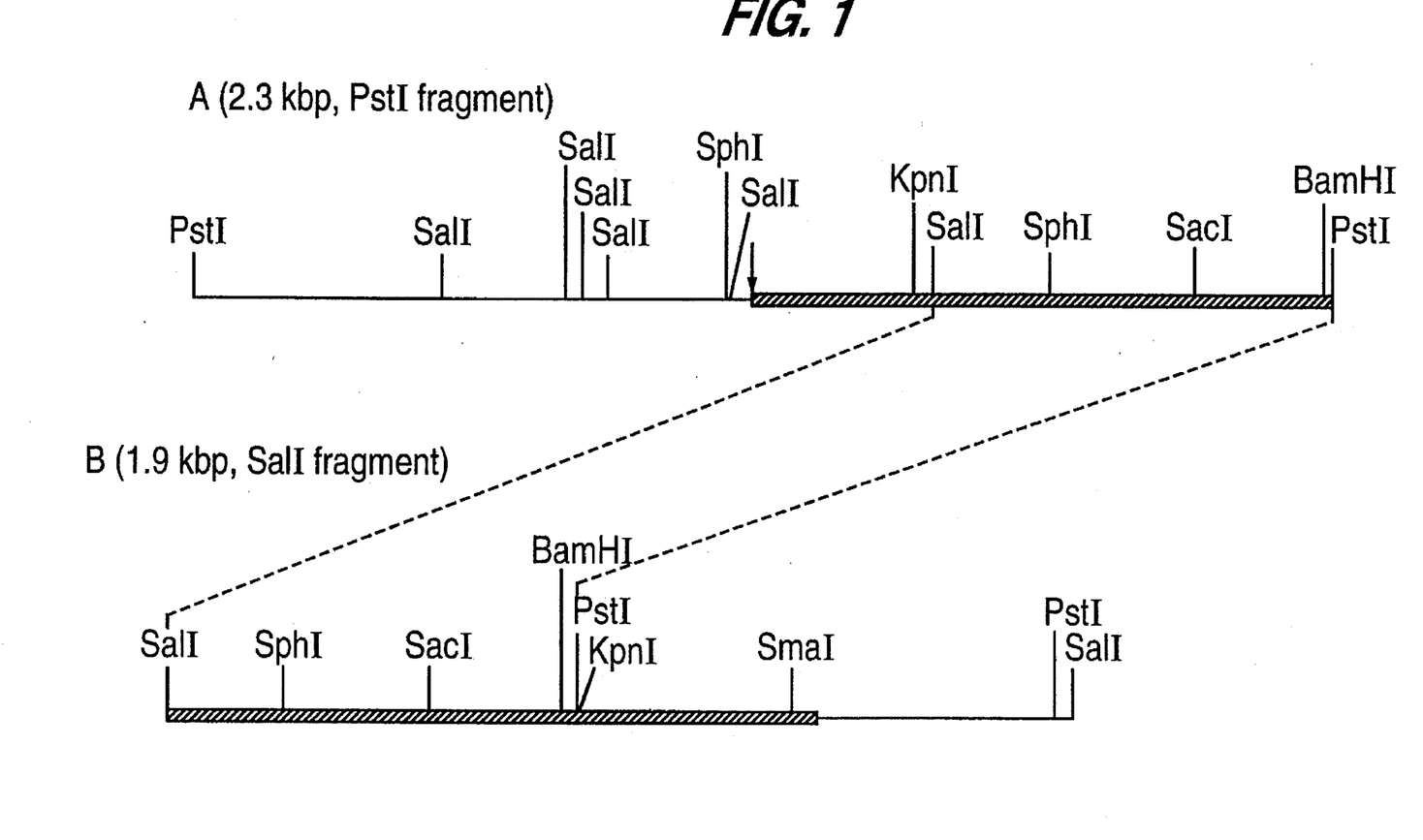

Plasmid DNAs of these clones were prepared by the alkaline lysis method and named respectively pUFSEP54, pUFSES30 and pUFSES68. These DNAs were digested with several restriction enzymes and the cleavage patterns were analyzed by electrophoresis. Thus it was confirmed that restriction enzyme sites (BamHI, KpnI, SacI, SmaI, etc.) existed therein: As the result of this analysis, it was revealed that the plasmid pUFSES30 was identical with the plasmid pUFSES68. Accordingly, pUFSEP54 and pUFSES30 were employed in the subsequent experiments. It was estimated that the inserts of pUFSEP54 and pUFSES30 had a sequence of about 800 bp in common. These clones were digested with appropriate restriction enzymes and subjected to self ligation by using a ligation kit (DNA Ligation Kit, manufactured by Takara Shuzo Co., Ltd.) to thereby give various deletion mutants. When the nucleotide sequences of these mutants were determined by the dideoxy method, an open reading frame of 1689 bp in size was found out in the inserts over two clones. The known amino acid sequences of α-1,3/4-fucosidase were all observed in this open reading frame. On the basis of these results, the full nucleotide sequence and the primary structure of the α-1,3/4-fucosidase gene were determined. FIG. 1 shows the result. A is the restriction enzyme map of the PstI fragment of 2.3 kb in size while B is the restriction enzyme map of the SalI fragment of 1.9 kb in size. The location of the α-1,3/4-fucosidase gene is also shown in this figure wherein the arrow indicates the start of the coding region, the thick line represents a coding region of α-1,3/4-fucosidase, and the part between SalI and PstI in the thick line in A corresponds to the part between SalI and PstI in the thick line in B. Thus the full length of the α-1,3/4-fucosidase gene can be found by combining A with B. A nucleotide sequence coding for α-1,3/4-fucosidase is shown in SEQ ID NO. 2 and an amino acid sequence coded for by this base sequence is shown by SEQ ID NO. 1.

EXAMPLE 2

Construction of Plasmids Expressing α-1,3/4-Fucosidase (1) Construction of Plasmids Coding for Polypeptide on the N-Terminal Side of α-1,3/4-Fucosidase In order to amplify a gene coding for a polypeptide on the N-terminal side of α-1,3/4-fucosidase, two synthetic oligonucleotide primers FSE-HNde (SEQ ID NO. 21) and S30RV (SEQ ID NO. 22) were designed and synthesized. The primer FSE-HNde was a 34mer having HindIII and NdeI sites in the downstream of an 18mer which corresponded to the sequence of base nos. 136 to 153 (in the 5'–3' direction) in the nucleotide sequence shown by SEQ ID NO. 2. On the other hand, the primer S30RV was a synthetic DNA of a 19mer which corresponded to the sequence of base nos. 443 to 461 (in the 3'–5' direction) in the nucleotide sequence shown by SEQ ID NO. 2.

About 100 pg of the plasmid pUFSEP54 obtained in the above Example 1, which was used as a template, was mixed with 10 μl of a buffer for amplification at 10-fold concentration in GeneAmp PCR Reagent Kit (manufactured by Takara Shuzo Co., Ltd.), 16 μl of a 1.2 mM dNEP mixture, 20 pmol of the primer FSE-HNde, 20 pmpol of the primer S30RV and 2.5 U Ampli Taq. To the obtained mixture was added sterilized water in such an amount as to give a total volume of 100 μl. Then this mixture was subjected to amplification by using an automated gene amplifier (DNA Thermal Cycler). The PCR was performed for 25 cycles with each cycle consisting of 30 seconds at 94° C. (denaturation), 1 minute at 55° C. (annealing of the primers) and 1.5 minutes at 72° C. (synthesis reaction). A 10 µl portion of the reaction mixture was electrophoresed on a 3% agarose gel and the DNA was stained with ethidium bromide to thereby ascertain the existence of an amplified DNA fragment of 342 bp which had been expected. The residue of the PCR mixture was concentrated by precipitating from ethanol and divided into two portions. One of these portions was cleaved with HindIII and SalI and inserted in between the HindIII and SalI sites of pTV119NNde [prepared by transforming the NcoI site of pTV119N (manufactured by Takara Shuzo Co., Ltd.) into an NdeI site]. Another portion was cleaved with NdeI and SalI and inserted in between the NdeI and SalI sites of pTV119NNde. These plasmids were named respectively pTFSEF101N and pTFSEM101N. Each plasmid was transformed into *Escherichia coli* JM109 employed as a host and the plasmid DNA was prepared by the alkaline lysis method. Subsequently, the insert was confirmed by PCR and the nucleotide sequence of the insert was determined by the dideoxy chain terminator method.

(2) Construction of Plasmid Coding for the Full Length of α-1,3/4-Fucosidase Gene The plasmid pUFSES30 obtained in the above Example 1 was digested with SalI and electrophoresed on an agarose gel. A SalI fragment of 1.9 kb in size was cut off, extracted and purified. Next, the plasmid pTFSEM101N obtained in the above Example 2-(1) was digested with SalI and the SalI fragment of 1.9 kb was inserted thereinto followed by the transformation into *Escherichia coli* JM109. The plasmid DNA was prepared by the alkaline lysis method and the regeneration of the SalI site was confirmed by the digestion with SalI. Next, the direction of the insert was confirmed by the digestion with SacI. The obtained plasmid coding for the full length of the α-1,3/4-fucosidase gene was named pTF-SEM201. Similarly, the plasmid pTFSEF101N obtained in the above Example 2-(1) was digested with SalI and a plasmid pTFSEF201 having the SalI fragment of 1.9 kb inserted thereinto was constructed. This plasmid contained a sequence coding for 10 amino acid residues (Met Ala Met Ile Thr Pro Ser Phe His Met; SEQ ID NO. 23) involving a peptide originating in lacZα in the upstream of the N-terminal of α-1,3/4-fucosidase. Thus it is expected that the expression of α-1,3/4-fucosidase in the form of a fused protein with lacZα would be induced by using the SD sequence of lacZ and the initiation codon thereof.

*Escherichia coli* JM109 having pTFSEM201 introduced thereinto is designated as *Escherichia coli* JM109/pTFSEM201. *Escherichia coli* JM109 having pTFSEF201 introduced thereinto is designated as *Escherichia coli* JM109/pTFSEF201 and has been deposited since Mar. 3, 1994 as FERM P-14206 at National Institute of Bioscience and Human-Technology, Agency of Industrial Science and Technology, of 1–3, Higashi 1-chome, Tsukuba-shi, Ibaraki-ken 305, Japan. Since Dec. 21, 1994, it has been deposited under the Budapest Treaty as FERM BP-4950 at National Institute of Bioscience and Human-Technology.

EXAMPLE 3

Expression of Recombinant α-1,3/4-Fucosidase in *Escherichia Coli*

(1) Expression of α-1,3/4-Fucosidase Polypeptide in *Escherichia Coli*

*Escherichia coli*JM109/pTFSEM201 or *Escherichia coli* JM109/pTFSEF201 obtained in the above Example 2 was inoculated into 5 ml of an L medium containing 100 µg/ml ampicillin and cultivated therein under shaking at 37° C. overnight. Then 1% of the culture was newly inoculated into 5 ml of the same medium. When the turbidity (absorbance at 600 nm) of the culture medium reached about 0.5, IPTG was added to the culture in such an amount as to give a final concentration of 1 mM and the cultivation was continued under shaking at 37° C. overnight. After the completion of the cultivation, 100 µl of the culture medium was centrifuged to thereby collect the cells. Then the cells were washed with a 50 mM potassium phosphate buffer (pH 6.0), suspended in 100 ml of the same buffer and disrupted by sonication. The suspension was centrifuged and the supernatant was recovered for use as an *Escherichia coli* extract. This extract and the precipitate were analyzed by SDS polyacrylamide gel electrophoresis. As a result, a band which was seemingly assignable to α-1,3/4-fucosidase of about 55,000 in molecular weight was observed in the extract and the precipitate originating in *Escherichia coli* JM109/pTFSEF201 and therefore it was ascertained that the α-1,3/4-fucosidase protein had been expressed therein. On the other hand, it was revealed that the enzyme protein had been scarcely expressed in *Escherichia coli* JM109/pTFSEM201. Accordingly, the α-1,3/4-fucosidase activity of the cell extract of *Escherichia coli* JM109/pTFSEF201 was assayed in accordance with the method described in Journal of Biological Chemistry, 267, (3), 1522–1527 (1992). As a result, it was found out that the cell extract of *Escherichia coli* JM109/pTFSEF201 had an activity of about 1 mU per ml of the culture medium. Although *Escherichia coli* JM109 strains carrying pTV119Nde not coding for the α-1,3/4-fucosidase structural gene and pTEFSEF101N coding exclusively for the N-terminal part were treated in the same manner, no α-1,3/4-fucosidase activity was observed therein. Based on these results, it is considered that the major part of the α-1,3/4-fucosidase produced by *Escherichia coli* JM109/pTFSEF201 has been insolubilized in the form of an inclusion body.

(2) Expression of α-1,3/4-Fucosidase in Escherichia Coli and Purification of Inclusion Body

*Escherichia coli* JMI109/pTFSEF201 was inoculated into 10 ml of an L medium containing 100 µg/ml ampicillin and cultivated under shaking at 37° C. for 5 hours. Then a 5 ml portion of this culture medium was inoculated into 500 ml of the same medium contained in a 2-1 Erlenmeyer flask and cultivated under shaking at 100 rpm at 37° C. When the turbidity (absorbance at 660 nm) of the culture medium reached about 0.5, IPTG was added to the culture in such an amount as to give a final concentration of 1 mM and the cultivation was continued under shaking at 37° C. overnight. After the completion of the cultivation, the cells were collected by centrifuging and suspended in 30 ml of a 10 mM Tris-HCl buffer (pH 8.0) containing 0.1M NaCl and 1 mM EDTA followed by the disruption through sonication. Then the disrupted cell suspension was centrifuged and the insoluble fractions containing the inclusion body were combined and suspended in 20 ml of a 1M sucrose solution. The suspension was centrifuged at 18,000×g for 30 minutes to thereby give a precipitate containing the inclusion body. Then it was suspended in 40 ml of a 2% solution of Triton X-100 containing 10 mM EDTA and allowed to stand at 4° C. overnight. After collecting the insoluble matters by centrifugation, the above procedure was repeated to thereby wash the inclusion body. A portion of the inclusion body thus obtained was analyzed by SDS polyacrylamide gel electrophoresis. As a result, more than a half of the proteins was electrophoresed at a position corresponding to a molecular weight of about 55,000. Thus it was assumed that the protein in more than a half of the inclusion body fraction obtained above comprised α-1,3/4-fucosidase. Compared with the band of bovine serum albumin analyzed simultaneously, it was estimated that this α-1,3/4-fucosidase protein could be obtained at least in an amount of 10 mg per 1 of the culture medium.

(3) Solubilization and Refolding of Inclusion Body

A 1/10 portion (corresponding to 100 ml of the culture medium) of the inclusion body obtained above was suspended in 1 ml of a 10 mM potassium phosphate buffer (pH 6.0) containing 8M urea and 10 mM dithiothreitol and solubilized by stirring at room temperature for 1 hour. After removing the insoluble matters remaining therein by centrifugation, the same buffer was added to the supernatant in such a manner as to give a total volume of 5 ml. Then it was introduced into a dialysis tube with a cut-off molecular weight of 10,000 and dialyzed against a 20 mM potassium phosphate buffer (pH 6.0) containing 0.6M KCl at 15° C. overnight. The retentate was centrifuged to thereby remove the insoluble matters and thus 7 ml of a supernatant was obtained. The α-1,3/4-fucosidase activity of this solution was assayed in accordance with the method described in Journal of Biological Chemistry, 267 (3), 1522–1527 (1992). As a result, it was found out that this supernatant had an activity of about 10 mU/ml. It was therefore found out that about 14 U of the recombinant α-1,3/4-fucosidase was obtained from 1 l of the culture medium of *Escherichia coli* JM109/PTFSEF201 having the gene of the present invention.

(4) Substrate Specificity of Recombinant α-1,3/4-Fucosidase

10 µl of the enzyme solution obtained in the above Example 3-(3) was added to a 30 mM potassium phosphate buffer (pH 6.0) containing 100 pmol pyridylaminated (PA-) lacto-N-fucopentaose (manufactured by Takara Shuzo Co., Ltd.) and reacted at 37° C. overnight. The reaction mixture was then freeze-dried and subjected to pyridylamination with the use of Glyco TAG (manufactured by Takara Shuzo Co., Ltd.). Then the obtained reaction mixture was analyzed for monosaccharides by using an anion exchange HPLC column. Thus it could be ascertained that fucose had been liberated from the substrate PA-lacto-N-fucopentaose.

By using various pyridylaminated oligosaccharides as a substrate, the α-1,3/4-fucosidase activities were assayed in accordance with the method described in Journal of Biological Chemistry, 267 (3), 1522–1527 (1992). Thus it was found out that this recombinant enzyme was specific for α1,3- and α1,4-fucoside bonds but exerted any action neither on α1,2-fucoside nor α1,6-fucoside bond. It also exerted scarcely any action on α2,3-sialyllacto-N-fucopentaose II. This substrate specificity was completely the same as that of α1,3/4-fucosidase of Streptomyces sp. 142.

Based on these results, the amino acid sequence and nucleotide sequence of α-1,3/4-fucosidase have been clarified for the first time by the present invention, which makes it possible to provide an α-1,3/4-fucosidase gene. Also, the present invention provides an industrially advantageous process for producing a polypeptide having the α-1,3/4-fucosidase activity by genetic engineering. According to the present invention, a high productivity of this enzyme can be achieved without requiring any induction by use of L-fucose. In addition, the present invention provides targets whereby the presence of α-1,3/4-fucosidase or the expression of the same can be examined, which makes it possible to prepare probes and primers based on these nucleotide sequences or to prepare antibodies based on the amino acid sequences.

What is claimed is:

1. An isolated α-1,3/4-fucosidase gene coding for an α-1,3/4-fucosidase comprising the amino acid sequence shown in SEQ ID No. 1.

2. An isolated α-1,3/4-fucosidase gene as set forth in claim having the DNA sequence shown in SEQ ID No. 2.

3. An isolated α-1,3/4-fucosidase gene which hybridizes with the gene as claimed in claim 1 under stringent conditions.

4. An isolated α-1,3/4-fucosidase gene which hybridizes with the gene as claimed in claim 2 under stringent conditions.

5. A recombinant plasmid containing the α-1,3/4-fucosidase gene as set forth in claim 1.

6. A recombinant plasmid containing the α-1,3/4-fucosidase gene as set forth in claim 2.

7. An isolated host cell comprising a recombinant plasmid containing the α-1,3/4-fucosidase gene as set forth in claim 1.

8. An isolated host cell comprising a recombinant plasmid containing the α-1,3/4-fucosidase gene as set forth in claim 2.

9. A process for producing α-1,3/4-fucosidase, comprising cultivating an isolated host cell into which a recombinant plasmid containing the α-1,3/4-fucosidase gene as set forth in claim 1 has been introduced to produce the α-1,3/4-fucosidase encoded thereby, and harvesting the α-1,3/4-fucosidase from the culture.

10. A process for producing α-1,3/4-fucosidase, comprising cultivating an isolated hast cell into which a recombinant plasmid containing the α-1,3/4-fucosidase gene as set forth in claim 2 has been introduced to produce the α-1,3/4-fucosidase encoded thereby, and harvesting the α-1,3/4-fucosidase from the culture.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 563 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

| Met | Ala | Arg | Arg | Thr | Arg | Val | Leu | Ser | Ala | Ile | Ala | Leu | Ala | Ala |
|---|---|---|---|---|---|---|---|---|---|---|---|---|---|---|
| 1 | | | | 5 | | | | | 10 | | | | | 15 |
| Ala | Ala | Ala | Leu | Val | Pro | Val | Gln | Ala | Thr | Ala | Gln | Gln | Ala | Ala |
| | | | | 20 | | | | | 25 | | | | | 30 |
| Pro | Ala | Ala | Ala | Gln | Gln | Pro | Gly | His | Arg | Ala | Ala | Ala | Pro | Pro |
| | | | | 35 | | | | | 40 | | | | | 45 |
| Gly | Thr | Pro | Cys | Ala | Ala | Pro | Val | Lys | Pro | Ala | Ser | Gln | Met | Ala |
| | | | | 50 | | | | | 55 | | | | | 60 |
| Val | Glu | Ser | Cys | Asp | Ser | Pro | Glu | Arg | Ile | Ile | Glu | Lys | Ala | Ala |
| | | | | 65 | | | | | 70 | | | | | 75 |
| Asn | Ile | Val | Pro | Thr | Ser | Gly | Gln | Leu | Ala | Trp | Gln | Gln | Arg | Glu |
| | | | | 80 | | | | | 85 | | | | | 90 |

```
Val  Thr  Ala  Phe  Thr  His  Phe  Gly  Met  Asn  Thr  Phe  Thr  Gly  Arg
                    95                  100                      105

Glu  Trp  Gly  Ser  Gly  Thr  Glu  Asp  Glu  Lys  Leu  Phe  Ala  Pro  Lys
                    110                 115                      120

Ser  Ile  Asp  Val  Asp  Gln  Trp  Met  Arg  Ala  Tyr  Lys  Ala  Ala  Gly
                    125                 130                      135

Ala  Glu  Gln  Val  Met  Leu  Thr  Ala  Lys  His  His  Asp  Gly  Phe  Val
                    140                 145                      150

Leu  Tyr  Pro  Ser  Arg  Tyr  Thr  Asp  His  Ser  Val  Glu  Leu  Ser  Pro
                    155                 160                      165

Gly  Ser  Pro  Asp  Val  Val  Gly  Ala  Tyr  Val  Lys  Ala  Ala  Arg  Lys
                    170                 175                      180

Ala  Gly  Leu  Lys  Val  Gly  Leu  Tyr  Leu  Ser  Pro  Ser  Asp  Gly  Ala
                    185                 190                      195

Glu  Leu  Pro  His  Ala  Trp  His  Ala  Gln  Trp  Val  Glu  Ser  Ile  Arg
                    200                 205                      210

Lys  Lys  Gln  Ala  Glu  Gly  Lys  Pro  Leu  Ser  Leu  Pro  Glu  Gln  Met
                    215                 220                      225

Ala  Leu  Glu  Asp  Gly  Asp  Arg  Ala  Pro  Ala  Gly  Glu  Gly  Arg  Phe
                    230                 235                      240

Gly  Asn  Gly  Ser  Ala  Val  Thr  Glu  Arg  Thr  Ile  Pro  Thr  Leu  Val
                    245                 250                      255

Pro  Gly  Asp  Asp  Arg  Ala  Ala  Ala  Val  Lys  Arg  His  Lys  Leu  Pro
                    260                 265                      270

Thr  Phe  Thr  Val  Met  Ala  Asp  Asp  Tyr  Asp  Ala  Tyr  Tyr  Leu  Asn
                    275                 280                      285

Gln  Leu  Tyr  Glu  Ile  Phe  Thr  Gln  Tyr  Gly  Pro  Ile  Glu  Glu  Leu
                    290                 295                      300

Trp  Leu  Asp  Gly  Ala  Asn  Pro  Trp  Ser  Gly  Ser  Gly  Ile  Thr  Gln
                    305                 310                      315

Lys  Tyr  Asn  Val  Lys  Gln  Trp  Phe  Asp  Met  Val  Lys  Ala  Leu  Ser
                    320                 325                      330

Pro  Asn  Thr  Val  Val  Phe  Gln  Gly  Pro  Gln  Gly  Val  Arg  Trp  Val
                    335                 340                      345

Gly  Asn  Glu  Gly  Gly  Thr  Ala  Arg  Glu  Thr  Glu  Trp  Ser  Val  Thr
                    350                 355                      360

Pro  His  Ala  Thr  Asp  Pro  Trp  Thr  Gly  Leu  Gly  Ser  Leu  Pro  Asn
                    365                 370                      375

Asp  Ser  Thr  Asp  Ala  Asp  Ile  Gly  Ser  Arg  Ala  Arg  Ile  Leu  Asp
                    380                 385                      390

Pro  Thr  Thr  Lys  Tyr  Leu  Gln  Trp  Tyr  Pro  Ala  Glu  Ala  Asp  Val
                    395                 400                      405

Ser  Ile  Arg  Pro  Gly  Trp  Phe  Tyr  His  Pro  Glu  Gln  Gln  Pro  Lys
                    410                 415                      420

Thr  Ala  Pro  Gln  Leu  Met  Asn  Leu  Tyr  Glu  Lys  Ser  Val  Gly  Arg
                    425                 430                      435

Asn  Ala  Ala  Leu  Leu  Leu  Asn  Val  Pro  Pro  Gly  Arg  Asp  Gly  Arg
                    440                 445                      450

Ile  Ala  Asp  Ala  Asp  Val  Ala  Ser  Leu  Thr  Ala  Phe  Gly  Lys  Ala
                    455                 460                      465

Val  Arg  Ser  Thr  Tyr  Gly  Thr  Asp  Val  Arg  Arg  Thr  Gln  Ala  Pro
                    470                 475                      480

Gly  Pro  Tyr  Thr  Phe  Asp  Arg  Val  Ala  Val  Arg  Glu  Asp  Ile  Arg
```

|   |   |   |   | 485 |   |   |   | 490 |   |   |   | 495 |
|---|---|---|---|---|---|---|---|---|---|---|---|---|
| His | Gly | Gln | Arg | Val | Glu | Lys | Phe | Ala | Val | Glu | Ala | Arg | Ile | Asp |
|   |   |   |   | 500 |   |   |   | 505 |   |   |   | 510 |
| Gly | Ser | Trp | Gln | Arg | Ile | Ala | Glu | Gly | Thr | Thr | Ile | Gly | Asn | Arg |
|   |   |   |   | 515 |   |   |   | 520 |   |   |   | 525 |
| Arg | Ile | Leu | Ser | Leu | Ala | Ser | Pro | Val | Thr | Ala | Thr | Ala | Val | Arg |
|   |   |   |   | 530 |   |   |   | 535 |   |   |   | 540 |
| Val | Lys | Val | Leu | Glu | Ser | Arg | Ala | Thr | Pro | His | Leu | Gly | Ala | Thr |
|   |   |   |   | 545 |   |   |   | 550 |   |   |   | 555 |
| Thr | Leu | His | Leu | Ser | Ser | Thr | Gly |
|   |   |   |   | 560 |

(2) INFORMATION FOR SEQ ID NO:2:

(i) SEQUENCE CHARACTERISTICS:
     (A) LENGTH: 1689 base pairs
     (B) TYPE: nucleic acid
     (C) STRANDEDNESS: double
     (D) TOPOLOGY: linear (ii) MOLECULE TYPE: genomic DNA (xi) SEQUENCE DESCRIPTION: SEQ ID NO:2:

| ATGGCACGAC | GCACCCGTGT | GCTCAGTGCG | ATCGCACTGG | CTGCCGCGGC | CGCGCTCGTT | 60 |
| CCCGTGCAGG | CCACCGCTCA | GCAAGCCGCG | CCGGCGGCCG | CGCAGCAGCC | CGGACATCGG | 120 |
| GCCGCCGCAC | CGCCTGGCAC | CCCGTGCGCC | GCGCCTGTGA | AGCCTGCTTC | GCAGATGGCC | 180 |
| GTGGAGTCCT | GCGACAGCCC | CGAGCGGATC | ATCGAGAAGG | CCGCGAACAT | AGTCCCCACC | 240 |
| TCCGGCCAAC | TCGCCTGGCA | GCAGCGGGAA | GTCACCGCCT | TCACCCACTT | CGGCATGAAC | 300 |
| ACCTTCACGG | GCCGCGAATG | GGGATCGGGT | ACCGAGGACG | AAAAGCTCTT | CGCCCCGAAG | 360 |
| AGCATCGACG | TCGACCAGTG | GATGCGCGCC | TACAAGGCGG | CCGGTGCCGA | GCAGGTCATG | 420 |
| CTCACCGCCA | AGCACCACGA | CGGGTTCGTC | CTGTACCCGT | CCGCTACACC | GACCACTCC | 480 |
| GTCGAACTCA | GCCCCGGCAG | CCCCGATGTC | GTCGGCGCCT | ACGTGAAGGC | CGCCCGTAAG | 540 |
| GCGGGCCTGA | AGGTCGGTCT | CTATCTCTCG | CCCTCCGACG | GCGCCGAACT | TCCGCACGCC | 600 |
| TGGCATGCCC | AGTGGGTCGA | GTCGATCCGC | AAGAAGCAGG | CGGAGGGCAA | GCCGCTGAGC | 660 |
| CTGCCCGAAC | AGATGGCGCT | GGAGGACGGC | GACCGGGCAC | CCGCGGGCGA | GGGCAGGTTC | 720 |
| GGCAACGGCA | GTGCCGTCAC | CGAGCGCACC | ATCCCCACCC | TCGTGCCCGG | CGACGACCGC | 780 |
| GCAGCCGCGG | TCAAGCGTCA | CAAGCTCCCC | ACCTTCACGG | TGATGGCCGA | CGACTACGAC | 840 |
| GCCTACTACC | TCAACCAGCT | GTACGAAATC | TTCACCCAGT | ACGGGCCGAT | CGAGGAGCTC | 900 |
| TGGCTGGACG | GCGCCAACCC | CTGGTCCGGC | TCCGGCATCA | CCCAGAAGTA | CAACGTCAAG | 960 |
| CAGTGGTTCG | ACATGGTCAA | GGCGCTGTCG | CCGAACACCG | TCGTCTTCCA | GGGCCCGCAG | 1020 |
| GGCGTGCGCT | GGGTCGGCAA | CGAGGGCGGG | ACCGCTCGTG | AGACCGAGTG | GAGCGTCACC | 1080 |
| CCGCACGCCA | CCGACCCATG | GACCGGGCTC | GGCAGCCTGC | CAACGACTC | GACCGACGCC | 1140 |
| GACATCGGCT | CCCGCGCCAG | GATCCTCGAC | CCGACGACCA | AGTACCTGCA | GTGGTACCCG | 1200 |
| GCCGAGGCGG | ACGTCTCCAT | CCGGCCCGGC | TGGTTCTACC | ACCCGGAACA | ACAACCCAAG | 1260 |
| ACTGCGCCGC | AGTTGATGAA | TCTGTACGAG | AAGAGCGTCG | GCCGGAACGC | CGCACTGCTG | 1320 |
| CTGAACGTGC | CGCCCGGCCG | GGACGGCCGG | ATCGCCGATG | CGGACGTCGC | GTCACTGACC | 1380 |
| GCCTTCGGCA | AGGCGGTGCG | CAGCACCTAC | GGCACCGATG | TGCGACGCAC | GCAGGCTCCG | 1440 |
| GGGCCGTACA | CCTTCGACCG | GGTCGCCGTC | CGCGAGGACA | TCCGGCACGG | GCAGCGGGTC | 1500 |

| GAGAAGTTCG | CCGTGGAGGC | CAGGATCGAC | GGCAGCTGGC | AGCGGATCGC | CGAGGGCACC | 1560 |
| ACGATCGGCA | ACCGGCGCAT | CCTGTCGCTC | GCCTCACCCG | TCACAGCGAC | GGCGGTACGG | 1620 |
| GTCAAGGTCC | TGGAGTCCCG | GGCCACACCT | CACCTCGGGG | CGACCACGCT | GCACCTGAGT | 1680 |
| TCGACCGGA | | | | | | 1689 |

(2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS: single
        (D) TOPOLOGY: linear     (ii) MOLECULE TYPE: peptide     (v) FRAGMENT TYPE: N-terminal fragment     (xi) SEQUENCE DESCRIPTION: SEQ ID NO:3:

```
Gly Thr Pro Cys Ala Ala Pro Val Lys Pro Ala Ser Gln Met Ala
 1               5                  10                  15
Val Glu Arg
```

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear     (ii) MOLECULE TYPE: peptide     (v) FRAGMENT TYPE: internal fragment     (xi) SEQUENCE DESCRIPTION: SEQ ID NO:4:

```
Leu Pro Thr Phe Thr Val Met Ala Asp Asp Tyr Asp Ala Tyr Tyr
 1               5                  10                  15
Leu Asn Gln Leu Tyr
                20
```

(2) INFORMATION FOR SEQ ID NO:5:

(i) SEQUENCE CHARACTERISTICS:
        (A) LENGTH: 26 bases
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:5:

CCSGCVWSHC ARATGGCNGT NGARMG          26

(2) INFORMATION FOR SEQ ID NO:6:

(i) SEQUENCE CHARACTERISTICS:
        (A) LENGTH: 26 bases
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:6:

TARTANGCRT CRTARTCRTC NGCCAT          26

( 2 ) INFORMATION FOR SEQ ID NO:7:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: other nucleic acid (synthetic DNA)

( x i ) SEQUENCE DESCRIPTION: SEQ ID NO:7:

ATGGCNGAYG AYTAYGAYGC    20

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal fragment     ( x i ) SEQUENCE DESCRIPTION: SEQ ID NO:8:

Ala Leu Ser Pro Asn Thr Val Cys Phe Gln Gly Pro Gln Val Arg
1               5                     10             15
Asp Val Gly Asn ( 2 ) INFORMATION FOR SEQ ID NO:9:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: other nucleic acid (synthetic DNA)

( x i ) SEQUENCE DESCRIPTION: SEQ ID NO:9:

TGYTTYCARG GNCCNCARGG    20

( 2 ) INFORMATION FOR SEQ ID NO:10:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: other nucleic acid (synthetic DNA)

( x i ) SEQUENCE DESCRIPTION: SEQ ID NO:10:

TGRAARCANA CNGTRTTNGG    20

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal fragment     ( x i ) SEQUENCE DESCRIPTION: SEQ ID NO:11:

| Ala | Cys | Asn | Ile | Val | Pro | Thr | Ser | Gly | Gln | Leu | Ala | Cys | Gln | Gln |
| 1 | | | | 5 | | | | | 10 | | | | | 15 |
| Arg | Glu | Val | Thr | Ala | | | | | | | | | | |
| | | | | 20 | | | | | | | | | | |

(2) INFORMATION FOR SEQ ID NO:12:

(i) SEQUENCE CHARACTERISTICS:
        (A) LENGTH: 20 bases
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:12:

TGYCARCARM GNGARGTNAC            20

(2) INFORMATION FOR SEQ ID NO:13:

(i) SEQUENCE CHARACTERISTICS:
        (A) LENGTH: 20 bases
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:13:

GTNGGNACDA TRTTRCANGC            20

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear     (ii) MOLECULE TYPE: peptide     (v) FRAGMENT TYPE: internal fragment     (xi) SEQUENCE DESCRIPTION: SEQ ID NO:14:

| Gln | Cys | Phe | Asp | Met | Val | Lys |
| 1 | | | | 5 | | |

(2) INFORMATION FOR SEQ ID NO:15:

(i) SEQUENCE CHARACTERISTICS:
        (A) LENGTH: 20 bases
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:15:

CARTGYTTYG AYATGGTNAA            20

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear     (ii) MOLECULE TYPE: peptide ( v ) FRAGMENT TYPE: internal fragment ( x i ) SEQUENCE DESCRIPTION: SEQ ID NO:16:

| Ser | Ile | Asp | Val | Asp | Gln | Cys | Met | Arg | Ala | Tyr | Lys |
|-----|-----|-----|-----|-----|-----|-----|-----|-----|-----|-----|-----|
| 1   |     |     |     | 5   |     |     |     |     | 10  |     |     |

( 2 ) INFORMATION FOR SEQ ID NO:17:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear     ( i i ) MOLECULE TYPE: other nucleic acid (synthetic DNA)

( x i ) SEQUENCE DESCRIPTION: SEQ ID NO:17:

TTGTABGCNC KCATRCA Y TG RTC      23

( 2 ) INFORMATION FOR SEQ ID NO:18:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: other nucleic acid (synthetic DNA)

( x i ) SEQUENCE DESCRIPTION: SEQ ID NO:18:

TTNACCATRT CRAARCA Y TG      20

( 2 ) INFORMATION FOR SEQ ID NO:19:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: other nucleic acid (synthetic DNA)

( x i ) SEQUENCE DESCRIPTION: SEQ ID NO:19:

GA Y GTNGA Y C ARTG Y AT-GMG      20

( 2 ) INFORMATION FOR SEQ ID NO:20:

( i ) SEQUENCE CHARACTERISTICS:
        ( A ) LENGTH: 140 base pairs
        ( B ) TYPE: nucleic acid
        ( C ) STRANDEDNESS: double
        ( D ) TOPOLOGY: linear     ( i i i ) MOLECULE TYPE: genomic DNA     ( x i ) SEQUENCE DESCRIPTION: SEQ ID NO:20:

TGTCAGCAGC GGGAGGTCAC CGCCTTCNCC CACTTCGGCA TGAACACCTT CACGGGCCGC      60

GAATGGGGAT CGGGTACCGA GGACGAAAAG CTCTTCGCCC CGAAGAGCAT CGACGTCGAT      120

CAATGTATGC GCGCGTACAA      140

( 2 ) INFORMATION FOR SEQ ID NO:21:

( i ) SEQUENCE CHARACTERISTICS:
        ( A ) LENGTH: 34 bases
        ( B ) TYPE: nucleic acid
        ( C ) STRANDEDNESS: single -continued ( D ) TOPOLOGY: linear ( i i ) MOLECULE TYPE: other nucleic acid (synthetic DNA)

( x i ) SEQUENCE DESCRIPTION: SEQ ID NO:21:

GCCAAGCTTT CATATGGGCA CCCCGTGCGC CGCG  34

( 2 ) INFORMATION FOR SEQ ID NO:22:

( i ) SEQUENCE CHARACTERISTICS:
      ( A ) LENGTH: 19 bases
      ( B ) TYPE: nucleic acid
      ( C ) STRANDEDNESS: single
      ( D ) TOPOLOGY: linear ( i i ) MOLECULE TYPE: other nucleic acid (synthetic DNA)

( x i ) SEQUENCE DESCRIPTION: SEQ ID NO:22:

GACGGGTACA GGACGAACC  19

( 2 ) INFORMATION FOR SEQ ID NO:23:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:23:

Met Ala Met Ile Thr Pro Ser Phe His Met
1           5                       10